(12) United States Patent
Duma et al.

(10) Patent No.: US 9,111,017 B2
(45) Date of Patent: Aug. 18, 2015

(54) PERSONAL INFORMATION SYSTEM

(75) Inventors: Christopher M. Duma, Newport Beach, CA (US); Kenneth L. Wright, San Clemente, CA (US); Chet La Guardia, Rancho Santa Margarita, CA (US)

(73) Assignee: DatCard Systems, Inc., Irvine, CA (US)

( * ) Notice: Subject to any disclaimer, the term of this patent is extended or adjusted under 35 U.S.C. 154(b) by 0 days.

(21) Appl. No.: 13/082,022

(22) Filed: Apr. 7, 2011

(65) Prior Publication Data

US 2011/0301981 A1 Dec. 8, 2011

Related U.S. Application Data

(63) Continuation of application No. 11/591,889, filed on Nov. 2, 2006, now Pat. No. 7,979,387, which is a continuation of application No. 09/781,605, filed on Feb. 12, 2001, now abandoned.

(60) Provisional application No. 60/181,985, filed on Feb. 11, 2000.

(51) Int. Cl.
*G06F 17/30* (2006.01)
*G06F 19/00* (2011.01)
(Continued)

(52) U.S. Cl.
CPC ............ *G06F 19/321* (2013.01); *G06F 19/323* (2013.01); *G06Q 50/24* (2013.01);
(Continued)

(58) Field of Classification Search
CPC ... G06F 19/321; G06F 19/322; G06F 19/323; G06F 19/3487
See application file for complete search history.

(56) References Cited

U.S. PATENT DOCUMENTS

| 4,149,239 A | 4/1979 | Jenkins et al. |
| 4,491,725 A | 1/1985 | Pritchard |

(Continued)

FOREIGN PATENT DOCUMENTS

| CA | 2322191 | 4/2000 |
| DE | 198 02 572 A1 | 8/1999 |

(Continued)

OTHER PUBLICATIONS

U.S. Appl. No. 09/540,531, filed Mar. 31, 2000, Shoji, et al.
(Continued)

*Primary Examiner* — Dinku Gebresenbet
(74) *Attorney, Agent, or Firm* — Knobbe Martens Olson & Bear LLP (57) ABSTRACT

The present invention provides systems and methods to realize the potential benefit of portable storage devices by taking advantage of standard PCs including an optical disk drive capable of reading an optical disk, such as a CD or a DVD, cost effective optical disks, and the Internet.

In a preferred embodiment, an individual patient provides personal data to a healthcare service center. The healthcare service center then creates a portable optical disk for the patient to carry, if he/she so desires. The personal data that is written onto the portable optical disk is stored on a database management server database and is readable and updateable by the individual patient using his/her PC with an optical disk drive and connected to the Internet. The individual patient can choose to update his/her personal data on the portable optical disk and can receive a new portable optical disk that includes the update. The new portable optical disk containing the latest update is created and delivered to the patient by the database management server.

19 Claims, 4 Drawing Sheets

(51) Int. Cl.
*G06Q 50/24* (2012.01)
*H04N 1/00* (2006.01)
*H04N 1/21* (2006.01)

(52) U.S. Cl.
CPC ......... *H04N1/00127* (2013.01); *H04N 1/2104* (2013.01); *G06F 19/322* (2013.01); *G06F 19/3418* (2013.01); *H04N 2201/3264* (2013.01); *H04N 2201/3266* (2013.01); *H04N 2201/3267* (2013.01); *H04N 2201/3277* (2013.01)

(56) References Cited

U.S. PATENT DOCUMENTS

| | | | |
|---|---|---|---|
| 4,736,256 A | 4/1988 | Ichikawa | |
| 4,852,570 A | 8/1989 | Levine | |
| 4,860,112 A | 8/1989 | Nichols et al. | |
| 4,874,935 A | 10/1989 | Younger | |
| 4,945,410 A | 7/1990 | Walling | |
| 4,958,283 A | 9/1990 | Tawara et al. | |
| 5,002,062 A | 3/1991 | Suzuki | |
| 5,005,126 A | 4/1991 | Haskin | |
| 5,019,975 A | 5/1991 | Mukai | |
| 5,208,802 A | 5/1993 | Suzuki et al. | |
| 5,235,510 A | 8/1993 | Yamada et al. | |
| 5,272,625 A | 12/1993 | Nishihara et al. | |
| 5,291,399 A | 3/1994 | Chaco | |
| 5,319,543 A * | 6/1994 | Wilhelm | 705/3 |
| 5,319,629 A | 6/1994 | Henshaw et al. | |
| 5,321,520 A | 6/1994 | Inga et al. | |
| 5,321,681 A | 6/1994 | Ramsay et al. | |
| 5,384,643 A | 1/1995 | Inga et al. | |
| 5,410,676 A | 4/1995 | Huang et al. | |
| 5,416,602 A | 5/1995 | Inga et al. | |
| 5,451,763 A | 9/1995 | Pickett et al. | |
| 5,469,353 A | 11/1995 | Pinsky et al. | |
| 5,499,293 A | 3/1996 | Behram et al. | |
| 5,513,101 A | 4/1996 | Pinsky et al. | |
| 5,531,227 A | 7/1996 | Schneider | |
| 5,542,768 A | 8/1996 | Rother et al. | |
| 5,544,649 A | 8/1996 | David et al. | |
| 5,572,422 A | 11/1996 | Nematbakhsh et al. | |
| 5,586,262 A | 12/1996 | Komatsu et al. | |
| 5,597,182 A | 1/1997 | Reber et al. | |
| 5,597,995 A | 1/1997 | Williams et al. | |
| 5,605,153 A | 2/1997 | Fujioka et al. | |
| 5,634,053 A | 5/1997 | Noble et al. | |
| 5,655,084 A | 8/1997 | Pinsky et al. | |
| 5,659,741 A | 8/1997 | Eberhardt | |
| 5,668,998 A | 9/1997 | Mason et al. | |
| 5,671,353 A | 9/1997 | Tian et al. | |
| 5,687,717 A | 11/1997 | Halpern et al. | |
| 5,721,825 A | 2/1998 | Lawson et al. | |
| 5,724,582 A | 3/1998 | Pelanek et al. | |
| 5,734,629 A | 3/1998 | Lee et al. | |
| 5,734,915 A | 3/1998 | Roewer | |
| 5,763,862 A | 6/1998 | Jachimowicz et al. | |
| 5,796,862 A | 8/1998 | Pawlicki et al. | |
| 5,809,243 A | 9/1998 | Rostoker et al. | |
| 5,822,544 A | 10/1998 | Chaco et al. | |
| 5,823,948 A | 10/1998 | Ross, Jr. et al. | |
| 5,832,488 A | 11/1998 | Eberhardt | |
| 5,848,198 A | 12/1998 | Penn | |
| 5,848,435 A | 12/1998 | Brant et al. | |
| 5,859,628 A | 1/1999 | Ross et al. | |
| 5,867,795 A | 2/1999 | Novis et al. | |
| 5,867,821 A * | 2/1999 | Ballantyne et al. | 705/2 |
| 5,869,163 A | 2/1999 | Smith et al. | |
| 5,873,824 A | 2/1999 | Doi et al. | |
| 5,882,555 A | 3/1999 | Rohde et al. | |
| 5,884,271 A | 3/1999 | Pitroda | |
| 5,899,998 A | 5/1999 | McGauley et al. | |
| 5,909,551 A | 6/1999 | Tahara et al. | |
| 5,911,687 A | 6/1999 | Sato et al. | |
| 5,914,918 A | 6/1999 | Lee et al. | |
| 5,920,317 A | 7/1999 | McDonald | |
| 5,924,074 A | 7/1999 | Evans | |
| 5,942,165 A | 8/1999 | Sabatini | |
| 5,946,276 A | 8/1999 | Ridges et al. | |
| 5,949,491 A | 9/1999 | Callahan et al. | |
| 5,950,207 A | 9/1999 | Mortimore et al. | |
| 5,982,736 A | 11/1999 | Pierson | |
| 5,995,077 A | 11/1999 | Wilcox et al. | |
| 5,995,345 A | 11/1999 | Overbo | |
| 5,995,965 A | 11/1999 | Experton | |
| 6,006,191 A | 12/1999 | DiRienzo | |
| 6,014,629 A * | 1/2000 | DeBruin-Ashton | 705/2 |
| 6,021,404 A | 2/2000 | Moukheibir | |
| 6,022,315 A | 2/2000 | Iliff | |
| 6,032,120 A | 2/2000 | Rock et al. | |
| 6,041,703 A | 3/2000 | Salisbury et al. | |
| 6,063,030 A | 5/2000 | Vara et al. | |
| 6,067,075 A | 5/2000 | Pelanek | |
| 6,109,324 A * | 8/2000 | Bugner et al. | 156/378 |
| 6,131,090 A | 10/2000 | Basso, Jr. et al. | |
| 6,148,331 A | 11/2000 | Parry | |
| 6,149,440 A | 11/2000 | Clark et al. | |
| 6,155,409 A | 12/2000 | Hettinger | |
| 6,157,914 A | 12/2000 | Seto et al. | |
| 6,241,668 B1 | 6/2001 | Herzog | |
| 6,260,021 B1 | 7/2001 | Wong et al. | |
| 6,272,470 B1 * | 8/2001 | Teshima | 705/3 |
| 6,278,999 B1 * | 8/2001 | Knapp | 1/1 |
| 6,283,761 B1 * | 9/2001 | Joao | 434/236 |
| 6,349,330 B1 * | 2/2002 | Bernadett et al. | 709/219 |
| 6,363,392 B1 | 3/2002 | Halstead et al. | |
| 6,397,224 B1 | 5/2002 | Zubeldia et al. | |
| 6,415,295 B1 | 7/2002 | Feinberg | |
| 6,421,650 B1 * | 7/2002 | Goetz et al. | 705/3 |
| 6,454,705 B1 | 9/2002 | Cosentino et al. | |
| 6,564,256 B1 | 5/2003 | Tanaka | |
| 6,564,336 B1 | 5/2003 | Majkowski | |
| 6,574,629 B1 | 6/2003 | Cooke, Jr. et al. | |
| 6,574,742 B1 | 6/2003 | Jamroga et al. | |
| 6,591,242 B1 | 7/2003 | Karp | |
| 6,633,674 B1 | 10/2003 | Barnes et al. | |
| 6,654,724 B1 | 11/2003 | Rubin et al. | |
| 6,671,714 B1 | 12/2003 | Weyer et al. | |
| 6,675,271 B1 | 1/2004 | Xu et al. | |
| 6,678,703 B2 | 1/2004 | Rothschild et al. | |
| 6,678,764 B2 | 1/2004 | Parvulescu et al. | |
| 6,934,698 B2 | 8/2005 | Judd | |
| 6,954,767 B1 | 10/2005 | Kanada | |
| 6,954,802 B2 | 10/2005 | Sutherland et al. | |
| 7,162,571 B2 | 1/2007 | Kilian et al. | |
| 7,213,022 B2 | 5/2007 | Whelan et al. | |
| 7,240,150 B1 | 7/2007 | Todd et al. | |
| 7,266,556 B1 | 9/2007 | Coates | |
| 7,298,836 B2 | 11/2007 | Wellons | |
| 7,366,836 B1 | 4/2008 | Todd et al. | |
| 7,379,605 B1 | 5/2008 | Ticsa | |
| 7,395,215 B2 | 7/2008 | Grushka | |
| 7,398,391 B2 | 7/2008 | Carpentier et al. | |
| 7,415,731 B2 | 8/2008 | Carpentier et al. | |
| 7,428,611 B1 | 9/2008 | Todd et al. | |
| 7,434,057 B2 | 10/2008 | Yagawa | |
| 7,475,432 B2 | 1/2009 | Carpentier et al. | |
| 7,487,551 B2 | 2/2009 | Carpentier et al. | |
| 7,523,489 B2 | 4/2009 | Bossemeyer et al. | |
| 7,530,115 B2 | 5/2009 | Carpentier et al. | |
| 7,539,813 B1 | 5/2009 | Todd et al. | |
| 7,546,486 B2 | 6/2009 | Slik et al. | |
| 7,552,340 B2 | 6/2009 | Ooi et al. | |
| 7,552,356 B1 | 6/2009 | Waterhouse et al. | |
| 7,590,672 B2 | 9/2009 | Slik et al. | |
| 7,591,022 B2 | 9/2009 | Carpentier et al. | |
| 7,621,445 B2 | 11/2009 | Esseiva et al. | |
| 7,640,271 B2 | 12/2009 | Logan, Jr. | |
| 7,657,581 B2 | 2/2010 | Orenstein et al. | |
| 7,694,331 B2 | 4/2010 | Vesikivi et al. | |
| 7,734,603 B1 | 6/2010 | McManis | |
| 7,797,546 B2 | 9/2010 | Kenson | |
| 7,836,493 B2 | 11/2010 | Xia et al. | |
| 8,045,214 B2 | 10/2011 | Samari | |
| 8,059,304 B2 | 11/2011 | Samari | |

(56) References Cited

U.S. PATENT DOCUMENTS

| | | | |
|---|---|---|---|
| 2001/0027402 A1* | 10/2001 | Ramsaroop | 705/2 |
| 2001/0041991 A1 | 11/2001 | Segal et al. | |
| 2001/0056359 A1 | 12/2001 | Abreu | |
| 2002/0010679 A1 | 1/2002 | Felsher | |
| 2002/0019751 A1 | 2/2002 | Rothschild et al. | |
| 2002/0046061 A1 | 4/2002 | Wright et al. | |
| 2002/0077861 A1 | 6/2002 | Hogan | |
| 2002/0083030 A1 | 6/2002 | Yang et al. | |
| 2002/0085476 A1 | 7/2002 | Samari-Kermani | |
| 2002/0103675 A1 | 8/2002 | Vanelli | |
| 2002/0103811 A1 | 8/2002 | Fankhauser et al. | |
| 2002/0133373 A1 | 9/2002 | Silva-Craig et al. | |
| 2002/0138524 A1 | 9/2002 | Ingle et al. | |
| 2003/0005464 A1 | 1/2003 | Gropper et al. | |
| 2003/0040940 A1 | 2/2003 | Nehammer | |
| 2003/0105393 A1* | 6/2003 | Sutherland et al. | 600/407 |
| 2003/0200226 A1 | 10/2003 | Wells et al. | |
| 2003/0208382 A1 | 11/2003 | Westfall | |
| 2003/0220822 A1 | 11/2003 | Fiala et al. | |
| 2004/0006492 A1 | 1/2004 | Watanabe | |
| 2004/0078236 A1 | 4/2004 | Stoodley et al. | |
| 2004/0083123 A1 | 4/2004 | Kim et al. | |
| 2004/0187012 A1 | 9/2004 | Kohiyama et al. | |
| 2004/0187027 A1 | 9/2004 | Chan | |
| 2004/0199762 A1 | 10/2004 | Carlson et al. | |
| 2004/0210458 A1 | 10/2004 | Evans et al. | |
| 2005/0075909 A1 | 4/2005 | Flagstad | |
| 2005/0086082 A1* | 4/2005 | Braunstein et al. | 705/2 |
| 2005/0125252 A1 | 6/2005 | Schoenberg et al. | |
| 2005/0125254 A1 | 6/2005 | Schoenberg | |
| 2005/0125258 A1 | 6/2005 | Yellin et al. | |
| 2005/0144172 A1 | 6/2005 | Kilian et al. | |
| 2005/0192837 A1 | 9/2005 | Fears et al. | |
| 2005/0197859 A1 | 9/2005 | Wilson et al. | |
| 2005/0240445 A1 | 10/2005 | Sutherland et al. | |
| 2005/0267863 A1 | 12/2005 | Carpentier et al. | |
| 2006/0080307 A1 | 4/2006 | Carpentier et al. | |
| 2006/0085226 A1 | 4/2006 | Kamber | |
| 2006/0155584 A1 | 7/2006 | Aggarwal | |
| 2006/0179112 A1 | 8/2006 | Weyer et al. | |
| 2006/0242144 A1 | 10/2006 | Esham et al. | |
| 2007/0027715 A1 | 2/2007 | Gropper | |
| 2007/0061170 A1 | 3/2007 | Lorsch | |
| 2007/0180509 A1 | 8/2007 | Swartz et al. | |
| 2008/0005030 A1 | 1/2008 | Schlarb et al. | |
| 2008/0013365 A1 | 1/2008 | Yueh | |
| 2008/0065718 A1 | 3/2008 | Todd et al. | |
| 2008/0071577 A1 | 3/2008 | Highley | |
| 2008/0183719 A1 | 7/2008 | Kageyama et al. | |
| 2008/0208919 A1 | 8/2008 | I Dalfo et al. | |
| 2008/0222654 A1 | 9/2008 | Xu et al. | |
| 2008/0244196 A1 | 10/2008 | Shitomi et al. | |
| 2008/0285759 A1 | 11/2008 | Shaw | |
| 2008/0313236 A1 | 12/2008 | Vijayakumar et al. | |
| 2008/0319798 A1 | 12/2008 | Kelley | |
| 2009/0043828 A1 | 2/2009 | Shitomi | |
| 2009/0055924 A1 | 2/2009 | Trotter | |
| 2009/0089335 A1 | 4/2009 | Shitomi et al. | |
| 2009/0119764 A1 | 5/2009 | Applewhite et al. | |
| 2009/0132775 A1 | 5/2009 | Otani et al. | |
| 2009/0157987 A1 | 6/2009 | Barley | |
| 2009/0198515 A1 | 8/2009 | Sawhney | |
| 2009/0204433 A1 | 8/2009 | Darian et al. | |
| 2009/0219411 A1 | 9/2009 | Marman et al. | |
| 2009/0240764 A1 | 9/2009 | Peleg et al. | |
| 2009/0252480 A1 | 10/2009 | Wright | |
| 2009/0319736 A1 | 12/2009 | Otani et al. | |
| 2010/0138446 A1 | 6/2010 | Canessa et al. | |
| 2010/0174750 A1 | 7/2010 | Donovan et al. | |
| 2010/0286997 A1 | 11/2010 | Srinivasan | |

FOREIGN PATENT DOCUMENTS

| | | |
|---|---|---|
| EP | 0 684 454 A1 | 11/1995 |
| EP | 0684565 | 11/1995 |
| EP | 0 781 032 A3 | 3/1999 |
| EP | 0 952 726 A1 | 10/1999 |
| GB | 2 096 440 A | 10/1982 |
| JP | 04-177473 A | 6/1992 |
| JP | 06-261892 A | 9/1994 |
| WO | WO 97/22297 | 6/1997 |
| WO | WO 00/02202 | 1/2000 |
| WO | WO 00/19416 | 4/2000 |
| WO | PCT/US01/04490 | 8/2009 |

OTHER PUBLICATIONS

U.S. Appl. No. 09/602,643, filed Jun. 22, 2000, Rothschild.
U.S. Appl. No. 09/761,795, filed Apr. 25, 2002, Kenneth L. Wright.
U.S. Appl. No. 09/781,605, filed Apr. 18, 2002, Kenneth L. Wright.
U.S. Appl. No. 11/942,630, filed Mar. 13, 2008, Kenneth L. Wright.
U.S. Appl. No. 90/009,347, filed Nov. 26, 2008, Kenneth L. Wright.
U.S. Appl. No. 60/181,215, filed Sep. 2, 2000, Segal.
U.S. Appl. No. 60/205,751, filed May 19, 2000, Samari-Kermani.
1996 Annual HIMSS Conference and Exhibition, Managing Care: The Race Is On, dated Mar. 3-7, 1996.
Dimitroff D.C. et al: "An Object Oriented Approach to Automating Patient Medical Records" Proceedings of the International Computer Software and Applications Conference. (Compsac), US, Washington, IEEE. Comp. Soc. Press, vol. CONF. 14, 1990, pp. 82-87.
FilmX Presentation slides.
Product Showcase: Automated Dicom Exchange Station, Medical Imaging Magazine, Jan. 2000.
"Security, ASP, Systems Integration to Highlight PACS Exhibits (Agfa through Amicas)," AuntMinnie.com, dated Nov. 26, 2000 (IDS U.S. Appl. No. 11/942,630) p. 20 #35.
"Security, ASP, Systems Integration to Highlight PACS Exhibits (InSiteOne through Rogan)," AuntMinnie.com, dated Nov. 16, 2000 (IDS U.S. Appl. No. 11/942,630) pp. 20 #36.
"Acuson Releases ViewPro-Net Network Image Review Software Package," Acuson Corp., dated Mar. 8, 1999. (IDS U.S. Appl. No. 11/942,630) pp. 52 #69.
"DICOM—Digital Imaging and Communications in Medicine," Presentations of the European Society of Cardiology (ESC), dated Aug. 25, 1999. (IDS U.S. Appl. No. 11/942,630) pp. 49 #22.
"Image Workstation DICOM Conformance Statement," Camtronics Medical Systems, Copyright 1999. (IDS U.S. Appl. No. 11/942,630) pp. 49 #15.
"SPEC, FUNC, TREXnet HR Image Network," Trex Medical Corp., 42 pages, revised Jan. 25, 2000.
"SPEC, FUNC, TREXnet HR, Phase I," Trex Medical Corp., 29 pages, revised Jan. 12, 1999.
"TDK Launches Innovative Medical DVD/CD Recording Station With Embedded PC," redOrbit.com, dated Sep. 13, 2004 (IDS U.S. Appl. No. 11/942,630) pp. 14 #42.
"Three-In-One: Siemens' SIENET MagicView 300 PACS Software Offers Image Distribution, Teleradiology and Mini-Archive," PRNewswire, Jun. 11, Copyright 1996-2008. (IDS U.S. Appl. No. 11/942,630) pp. #109.
10th Conference on Computer Applications to Assist Radiology and 4th Conference on Computer Assisted Radiology, RL Arenson & RM Friedenberg, Symposium Foundation, Copyright 1990, pp. 1-441.
10th Conference on Computer Applications to Assist Radiology and 4th Conference on Computer Assisted Radiology, RL Arenson & RM Friedenberg, Symposium Foundation, Copyright 1990, pp. 442-791.
11th Conference on Computer Applications in Radiology and 6th Conference on Computer assisted Radiology, William Brody and Gerald Johnston, Copyright 1992, pp. 1-375.
11th Conference on Computer Applications in Radiology and 6th Conference on Computer assisted Radiology, William Brody and Gerald Johnston, Copyright 1992, pp. 376-434; 445-749.
12th Conference on Computer Applications in Radiology and 8th Conference on Computer Assisted Radiology, Jun. 12-15, 1994, Johannes Boehme & Alan Rowberg, Copyright 1994.

(56) References Cited

OTHER PUBLICATIONS

13th Conference on Computer Applications in Radiology, Jun. 6-9, 1996, R Kilcoyne, et al., Copyright 1996.
A look at infoRAD 1992, infoRAD: Informatics in Radiology, Ackerman, Radiographics Sep. 1992, 12:5.
A PACS RFP toolkit presented to the Fifth RIS-PACS School, Georgetown University Medical Center, JH Perry, Dated Feb. 3, 1995.
A PACS RFP toolkit presented to the Seventh RIS-PACS School, Georgetown University Medical Center, JH Perry, Dated Aug. 11, 1997. (IDS U.S. Appl. No. 11/942,630) pp. 4 #44.
Accessing Picture Archiving and Communication System Text and Image Information Through Personal Computers, MR Ramaswamy et al., Computers in Radiology, AJR 163, Nov. 1994. (IDS U.S. Appl. No. 11/942,630) pp. 4 #46.
Accusoft, High-Performance Medical Imaging Software (1997).
Acom.Convert DICOM Conformance Statement, Siemens, dated Sep. 15, 1999.
ACOM.PC 2.2 DICOM Conformance Statement, Version1.0, dated Sep. 29, 1999.
Advantages of a Cardiac DICOM Network Server / Writer for Viewing and Permanent CD-R Archiving of Cardiovascular Angiography Images, Hibel et al, Computers in Cardiology 2000; 27:649-652. (IDS U.S. Appl. No. 11/942,630).
AGFA, Mini-PACS . . . A Product Comparison Chart.
AIM, Advanced informatics in medicine, EurIPACS, European integrated picture archiving & communication system in the hospital, Merheus et al., dated Dec. 31, 1994. (IDS U.S. Appl. No. 11/942,630) pp. 4 #49.
Algotec Systems Ltd., From Board Design to Multi-Modality Workstations. (IDS U.S. Appl. No. 11/942,630) pp. 55 #133.
Algotech, CDSurf, Help File, dated 1999.
Ali, DICOM WinView, Help File (IDS U.S. Appl. No. 11/942,630) pp. 33 #45.
American Society of Echocardiography, DICOM Demonstration, Toronto, Canada, dated Jun. 14-16, 1995 (IDS U.S. Appl. No. 11/942,630) pp. 33 #52.
Amit Mehta et al., "Enhancing Availability of the Electronic Image Record for Patients and Caregivers During Follow-Up Care," Journal of Digital Imaging, vol. 12, No. 2, pp. 78-80, May 1999. (IDS U.S. Appl. No. 11/942,630) pp. 50 #45.
Amit Mehta, Electronic Imaging Infrastructure Workflow.
Amit Mehta, Interpretation and Voice Recognition.
An economical, personal computer-based picture archiving and communication system, T-C Wu et al., Radiographics Mar.-Apr. 1999, 19:2.
Analogic, SuperDASM Configuration Keywords: A White Paper Engineering Document, Rev. 2, dated Jul. 13, 1998 (IDS U.S. Appl. No. 11/942,630) pp. 37 #117.
Angiocardiography without cinefilm: information on the new digital imaging interchange standard for cardiology based on DICOM, "Last Updated: Tuesday, Jun. 11, 1996 by Tim Becker."
Applicare Medical Imaging B.V., The RadWorks Product Line Version 2.1 Product Catalog (Summer 1997).
Areeda Associates Ltd, SeeMor: Image Viewing Software for Windows 95/NT and Macintosh.
Areeda Associates, SeeMor Users Manual, dated 1997 (IDS U.S. Appl. No. 11/942,630) pp. 34 #59.
Areeda Associates, SeeMor Version 3, "Apple Macintosh MacOS 8.x Users Manual" (IDS U.S. Appl. No. 11/942,630) pp. 45 #257.
Areeda Associates, SeeMor Version 3, "Windows 9X/2000/NT4 Users Manual," dated 1999 (IDS U.S. Appl. No. 11/942,630) pp. 45 #255.
ARRI Oscar Product Brochure, ARRI, Copyright 1999. (IDS U.S. Appl. No. 11/942,630) pp. 54 #115.
Atsutoshi Oka et al., "Interhospital Network System Using the Worldwide Web and the Common Gateway Interface," Journal of Digital Imaging, vol. 12, No. 2, pp. 205-207, May 1999. (IDS U.S. Appl. No. 11/942,630) pp. 51 #47.

Betsy S. Hersher, et al., "The CIO's Position in Today's Emerging Health Care System: Lessons Learned," 1996 Annual HIMSS Conference and Exhibition (IDS U.S. Appl. No. 11/942,630) pp. 43 #231.
Bradley J. Erickson et al., "READS: A Radiology-Oriented Electronic Analysis and Display Station," Journal of Digital Imaging, vol. 10, No. 3, pp. 67-69, Aug. 1997. (IDS U.S. Appl. No. 11/942,630) pp. 52 #71.
Brian L. Cassel, "Defining the Future Managed Care Information Requirements," 1996 Annual HIMSS Conference and Exhibition (IDS U.S. Appl. No. 11/942,630) pp. 39 #141.
Brian M. Paige, "Information Warehousing in the Integrated Delivery System," 1996 Annual HIMSS Conference and Exhibition (IDS U.S. Appl. No. 11/942,630) pp. 40 #176.
C.J. Henri et al., "Evolution of a Filmless Digital Imaging and Communications in Medicine—Conformant Picture Archiving and Communications System: Design Issues and Lessons Learned Over the Last 3 Years," Journal of Digital Imaging, vol. 12, No. 2, pp. 178-180, May 1999. (IDS U.S. Appl. No. 11/942,630) pp. 51 #48.
Camtronics, Ltd., Camtronics Medical Systems: Image Workstation: DICOM Conformance Statement: Document No. 09610-0021 (Rev. A), dated Oct. 26, 1999.
Capturing clinical reports in a large academic medical center: Feeding a central patient data repository, MK Ekstrom et al. (IDS U.S. Appl. No. 11/942,630) pp. 4 #54.
CD-Surf User's Guide Version 1.0, Algotec, Copyright 2001. pp. 4 #56.
Cindy D. Spurr, et al., "Automating Critical Pathways—One Hospital's Experience," 1996 Annual HIMSS Conference and Exhibition (IDS U.S. Appl. No. 11/942,630) pp. 43 #223.
Clement J. McDonald, MD, "Implementing a Physician Order Entry System: Perspectives From Five Physicians," 1996 Annual HIMSS Conference and Exhibition (IDS U.S. Appl. No. 11/942,630) pp. 41 #179.
Colleen M. Prophet, et al., "On the 'Paperless Trail'—A Computerized Charting System," 1996 Annual HIMSS Conference and Exhibition (IDS U.S. Appl. No. 11/942,630) pp. 40 #175.
Consulting with radiologist outside the hospital by using java, S-K Lee et al., Radiographics 19:4, Jul.-Aug. 1999.
Cynthia McKinney and Susan Brockhaus, "Benefits of Cost Accounting Within a Multihospital System," 1996 Annual HIMSS Conference and Exhibition pp. 40 #160.
Deborah Kohn, MPH, RRA et al., "Mail and Messaging Software: M&Ms of Communication—A Treat for Health Care Information Systems," 1996 Annual HIMSS Conference and Exhibition (IDS U.S. Appl. No. 11/942,630) pp. 42 #206.
Dennis Winstein, et al., "Optimizing Clinical Information Systems in Complex Computing Environments," 1996 Annual HIMSS Conference and Exhibition (IDS U.S. Appl. No. 11/942,630) pp. 40 #169.
DICOM Birmingham 96, Tutorial Rev. 3.0, dated 1996.
DICOM Structured Reporting, David Clunie, Copyright 2000. (IDS U.S. Appl. No. 11/942,630) pp. 5 #69.
DICOMwriter Product Webpage, Heartlab Inc., Copyright 1999. (IDS U.S. Appl. No. 11/942,630) pp. 50 #42.
Digital archive system for radiologic images, AWK Wong, et al., Radiographics 14:5, Sep. 1994.
Digital networking and archiving with ACOM TOP, W Sallfrank, International Journal of Cardiac Imaging 14:323-327, 1998.
Distributing medical images with internet technologies: A DICOM java viewer, J Fernandez-Bayo et al., Radiographics 20:2, Mar.-Apr. 2000.
Donald R. Cahill et al., "Sectional Anatomy Using the Personal Computer," Journal of Digital Imaging, vol. 10, No. 3, p. 227, Aug. 1997.
Draft Specifications for Medical Diagnostic Imaging Support (MDIS) System, Apr. 6, 1990 (IDS U.S. Appl. No. 11/942,630) pp. 21 #7.
Editorial, Wong and Huang, Computerized Medical Imaging and Graphics 20:4, Jul.-Aug. 1996. (IDS U.S. Appl. No. 11/942,630) pp. 5 #76.
Edward Barthell, et al., "The National Information Infrastructure Health Information Network NII-HIN," 1996 Annual HIMSS Conference and Exhibition (IDS U.S. Appl. No. 11/942,630) pp. 45 #253.

(56) References Cited

OTHER PUBLICATIONS

Etiam, DICOM 3.0 Conformance Statement: DICOM Eye v2.42 Version 1, dated Sep. 12, 2000 (IDS U.S. Appl. No. 11/942,630) pp. 15 #57.
Final Text—Supplement 2, Digital Imaging and Communications in Medicine (DICOM), Part 11: Media Storage Application Profiles, Addenda on Conformance, dated Feb. 26, 1995. (IDS U.S. Appl. No. 11/942,630) pp. 6 #82.
Final Text—Supplement 3—Part 12, Digital Imaging and Communications in Medicine (DICOM), Part 12: Media Format and Physical Media for Media Interchange, dated Feb. 26, 1995.
Finding the path: A worldwide web-based guide for imaging evaluation of patients in the emergency department, LM Azmoun et al., Radiographics 17:1, Jan.-Feb. 1997.
G. James Blaine, et al., "project Spectrum: Technology Alliance for the Emerging Integrated Health System," 1996 Annual HIMSS Conference and Exhibition (IDS U.S. Appl. No. 11/942,630) pp. 43 #217.
Gail S. Gulinson, "Transforming the Health Care System Through Health Data Networking," 1996 Annual HIMSS Conference and Exhibition (IDS U.S. Appl. No. 11/942,630) pp. 39 #145.
GE Medical Systems Technical Publications, Direction 2246811-100, Revision 2, Senographe 2000 D Acquisition Workstation Conformance Statement for DICOM V3.0, latest Copyright 2000.
GE Medical Systems Technical Publications, IIS FP10282, Revision 1, PathSpeed PACS Version 8.0 Conformance Statement for DICOM V3.0, Dated Sep. 2000. (IDS U.S. Appl. No. 11/942,630) pp. 6 #86.
GE Medical Systems, Cardio—Viewing Station—CD-R Wiedergabestation fur die digitale Zukunft (Article in German).
GE Medical Systems, Medical CD Recording Station.
Guardian DICOM Archive Media Storage Conformance Statement, DR Systems, Inc., dated May 4, 1999.
H.K. Huang, PACS: Basic Principles and Applications, Wiley, New York (1999).
Haveri, M., "medical-image-faq/volume-visualization," dated Nov. 23, 1998.
Haveri, M., "med-volviz-faq-2000-01" in Jun. 12, 2009.
Hipax Medical Imaging and Communication System Version 3 User Instruction Manual, Sep. 1999 (IDS U.S. Appl. No. 11/942,630) pp. 21 #12.
Image archives and image data bases: How do they differ?, CC Jaffe, Radiographics 14:3, May 1994. (IDS U.S. Appl. No. 11/942,630) pp. 6 #88.
ImagiNet Workflow and Management Manual Version 3.0, Algotec, Copyright 2003. (IDS U.S. Appl. No. 11/942,630) pp. 6 #89.
Imaging Resource, Kodak Picture CD, http://www.imagingresource.com/PRODS/PCD/PCDA.HTM (Nov. 10, 1999).
IMCO-RAD Digitizer Product Brochure, IMCO Tech., undated.
IMPAX Web 1000 DICOM Web Server Specifications, dated May 30, 1998 (IDS U.S. Appl. No. 11/942,630) pp. 14 #51.
Implementation of the DICOM 3.0 Standard: A pragmatic Handbook, Robert Hindel, Copyright 1994. (IDS U.S. Appl. No. 11/942,630) pp. 6 #90.
Implementing a DICOM-HL7 interface application, SL Fritz et al., SPIE vol. 2435. (IDS U.S. Appl. No. 11/942,630) pp. 6 #91.
Information management and distribution in a medical picture archive and communication system, FW Prior, Copyright 1992. pp. 6 #92.
Integrating the healthcare enterprise: A primer: Part 4. The role of existing standards in IHE, M Henderson et al., Radiographics 21:6, Nov.-Dec. 2001.
Jagdish Kohli, PhD, et al., "Distributed Architecture for a Wide-Area Medical Image Repository," 1996 Annual HIMSS Conference and Exhibition (IDS U.S. Appl. No. 11/942,630) pp. 41 #180.
James Kazmer et al., "The Creation of a Virtual Electronic Medical Record," 1996 Annual HIMSS Conference and Exhibition (IDS U.S. Appl. No. 11/942,630) pp. 42 #209.
Jan M. Kastens, RN, M.S., "Hospital Information Systems Approaches Do Not Work for Integrated Health Care Delivery," 1996 Annual HIMSS Conference and Exhibition (IDS U.S. Appl. No. 11/942,630) pp. 39 #146.

Jeffrey S. Blair, "An Overview of Health Care Information Standards," 1996 Annual HIMSS Conference and Exhibition (IDS U.S. Appl. No. 11/942,630) pp. 41 #181.
Jeffrey W. Muscarella and John Hoben, "Delivering Information Services Via the World Wide Web," 1996 Annual HIMSS Conference and Exhibition (IDS U.S. Appl. No. 11/942,630) pp. 44 #248.
Jerry L. Mathis et al., "Case Study: A Health Care System's Use of Wireless Technology," 1996 Annual HIMSS Conference and Exhibition (IDS U.S. Appl. No. 11/942,630) pp. 42 #203.
Kevin J. Dombkowski, et al., "Using Electronic Data Interchange in Managed Care Performance Measurement," 1996 Annual HIMSS Conference and Exhibition (IDS U.S. Appl. No. 11/942,630) pp. 41 #178.
Legacy System Integration Using Web Technology, RL Kennedy et al, Proc. Of SPIE vol. 3980, PACS Design and Evaluation: Engineering and Clinical Issues, dated Feb. 2000.
Letter from J. Hofmann re "MedImage—Digital Image and Document Management," 3 pages, Dec. 15, 1997.
Mark H. Biddle, Esq., et al., "Integrating Telecommunications Systems Into the Evolving Health Care Delivery Environment," 1996 Annual HIMSS Conference and Exhibition (IDS U.S. Appl. No. 11/942,630) pp. 40 #174.
Medasys Digital Systems, DICOM Conformance Statement (IDS U.S. Appl. No. 11/942,630) pp. 38 #132.
Medasys Digital Systems, Tutorial (IDS U.S. Appl. No. 11/942,630) pp. 38 #136.
Medcon Ltd, Medcon's Telecardiology and Networked Archiving System for Cardiac Cath Labs. (IDS U.S. Appl. No. 11/942,630) pp. 55 #135.
Med-e-Mail Technical Manual Version 1.0, Algotec, Copyright 2001. (IDS U.S. Appl. No. 11/942,630) pp. 7 #100.
Medical image databases: a content-based retrieval approach, Tagare et al., J Am Med Inform Assoc. 1997. (IDS U.S. Appl. No. 11/942,630) pp. 7 #101.
Medical Imaging Technology Associates, Preliminary Tapestry Users Guide, dated 1997 (IDS U.S. Appl. No. 11/942,630) pp. 32 #29.
Mediface, "PiView™ 3.0 User's Guide, part 1" dated Sep. 1999 (IDS U.S. Appl. No. 11/942,630) pp. 31 #9.
Mediface, "PiView™ 3.0 User's Guide, part 2" dated Sep. 1999 (IDS U.S. Appl. No. 11/942,630) pp. 31 #10.
Mediface, "PiView™ 3.0 User's Guide, part 3" dated Sep. 1999 (IDS U.S. Appl. No. 11/942,630) pp. 31 #11.
Mediface, PiView 3.0, "DICOM Conformance Statement, Rev. 1.2-990903," dated 1999 (IDS U.S. Appl. No. 11/942,630) pp. 32 #15.
MediLink Technical Manual Version 1.5, Algotec, Copyright 2001. (IDS U.S. Appl. No. 11/942,630) pp. 7 #102.
MedImage Image Management System DICOM Conformance Statement, Vepro, dated May 8, 2000.
MediPrime DICOM Conformance Statement, Algotec, Latest Copyright 2000. (IDS U.S. Appl. No. 11/942,630) pp. 7 #103.
MediStore Technical Manual Version 1.1, Algotec, Copyright 1999. (IDS U.S. Appl. No. 11/942,630) pp. 7 #104.
MediSurf Product Brochure, Algotec Systems, undated.
Medweb Image Server DICOM Conformance Statement, Revision 2.1, dated Jul. 1, 1998.
MergeWorks: A system of flexible building blocks that provide DICOM infrastructure for electronic image management, MergeTechnologies, Inc., "webarchive.org" date "Dec. 2, 1998."
Michael J. Cannavo, "PACS Integration: Info Network Integrates Islands of Automation," Diagnostic Imaging, pp. 25-27, dated Feb. 1998 (IDS U.S. Appl. No. 11/942,630) pp. 45 #271.
Micromedica, Sistema MICS—Medical Imaging Communication System.
Mitra CD Exchange Operator's Manual, dated 1997.
Multimedia image and data navigation workstation, O Ratib et al., Radiographics 17:2, Mar.-Apr. 1997.
OSIRIS, OSIRIS Imaging Software User Manual, Version 3.1, dated 1996 (IDS U.S. Appl. No. 11/942,630) pp. 33 #49.
PACS Implementation Experiences: From In-house to Partnership to Advisory Board, HK Huang, Proc. Of SPIE vol. 3980, PACS Design and Evaluation: Engineering and Clinical Issues, dated Feb. 2000.

(56) References Cited

OTHER PUBLICATIONS

PACS mini refresher course: Evaluation of requirements and planning for picture archiving and communication system, JC Honeyman et al., Radiographics 12:1, Jan. 1992.
Pacs mini refresher course: Introduction to the ACR-NEMA DICOM Standard, WD Bidgood & SC Horii, Radiographics 12:2, Mar. 1992.
PACS mini refresher course: Local area network topologies, media, and routing, BK Stewart., Radiographics 12:3, May 1992.
PACS mini refresher course: Network and ACR-NEMA DICOM protocols, SC Horii & WD Bidgood, Radiographics 12:3, May 1992.
PACS mini refresher course: Software suite for image archiving and retrieval, SR Seshadri et al., Radiographics 12:2, Mar. 1992.
PACS mini refresher course: Three methods of implementing a picture archiving and communication system, HK Huang, Radiographics 12:1, Jan. 1992.
PACS mini refresher course: Wide area network strategies for teleradiology system, SJ Dwyer et al., Radiographics 12:3, May 1992.
PACS: Picture archiving and communication systems in biomedical imaging, HK Huang, Copyright 1996, pp. 396-401 and Table of Contents (IDS U.S. Appl. No. 11/942,630) pp. 8 #128.
PACSPLUS, PACSPLUS Viewer User Manual: Version 2.1.4 (IDS U.S. Appl. No. 11/942,630) pp. 14 #47.
Philips Medical Systems, DICOM Conformance Statement—CD-Medical Recorder for DCI Systems CDM 3300—Release 1.1 (Oct. 31, 1996).
Product Showcase Webpage, Medical Imaging, Jan. 2000. (IDS U.S. Appl. No. 11/942,630) pp. 53 #96.
Product Showcase, "Automated DICOM Exchange Station" (Sorna Product Announcement), Medical Imaging Magazine, vol. 15, No. 1, Jan. 2000, p. 72 (IDS U.S. Appl. No. 11/942,630) pp. 22 #14.
Project DEPRAD (Deployable Radiology and Teleradiology System) in Bosnia/Hungary, SK Mun, Report Date Mar. 1997.
R. L. (Vern) Davenport, et al., "Understanding and Assessing CHIN Network Technology," 1996 Annual HIMSS Conference and Exhibition pp. 40 #168.
R.D. Cox et al., "Transparent Image Access in a Distributed Picture Archiving and Communications System: The Master Database Broker," Journal of Digital Imaging, vol. 12, No. 2, pp. 175-177, May 1999.
Radiology and computer science, LV Ackerman, Radiographics 11:6, Nov. 1991. (Mar. 16, 2010—IDS U.S. Appl. No. 12/484,064) pp. 8 #133.
Raffaele Noro et al., "Real-Time Telediagnosis of Radiological Images through an Asynchronous Transfer Mode Network: the ARTeMeD Project," Journal of Digital Imaging, vol. 10, No. 3, pp. 116-121, Aug. 1997. (IDS U.S. Appl. No. 11/942,630) pp. 51 #46.
Ralph T. Wakerly, et al., "Planning for the Four Stages of Health Information Network Development," 1996 Annual HIMSS Conference and Exhibition (IDS U.S. Appl. No. 11/942,630) pp. 41 #182.
Ramesh C. Verma et al., "Picture Archiving and Communication System—Asynchronous Transfer Mode Network in a Midsized Hospital," Journal of Digital Imaging, vol. 10, No. 3, pp. 99-102, Aug. 1997. (IDS U.S. Appl. No. 11/942,630) pp. 52 #73.
RDI, Cobrascan, Xscan32 Imaging Software, Version 2.10, Users' Guide, dated 1999 (IDS U.S. Appl. No. 11/942,630) pp. 38 #127.
RDI, Xscan32: The Total Imaging Software Solution, Presentation (IDS U.S. Appl. No. 11/942,630) pp. 37 #119.
Richard K. Wertz, "CD-ROM: A New Advance in Medical Information Retrieval," JAMA, vol. 256, No. 24, pp. 3376-3378, Dec. 26, 1986. (IDS U.S. Appl. No. 11/942,630) pp. 52 #79.
Richard P. Corley, et al., "Infrastructure Requirements for Rapidly Changing Hospital Delivery Systems," 1996 Annual HIMSS Conference and Exhibition (IDS U.S. Appl. No. 11/942,630) pp. 44 #236.
Ricky K. Taira et al., "A Concept-Based Retrieval System for Thoracic Radiology," Journal of Digital Imaging, vol. 9, No. 1, pp. 25-36, Feb. 1996. (IDS U.S. Appl. No. 11/942,630) pp. 52 #70.
Robert Bowman, et al., "Building and Maintaining Today's Networks," 1996 Annual HIMSS Conference and Exhibition (IDS U.S. Appl. No. 11/942,630) pp. 43 #227.
Rosemary Nelson, et al., "Outcomes of Telemedicine Services . . . Patient and Medicolegal Issues," 1996 Annual HIMSS Conference and Exhibition (IDS U.S. Appl. No. 11/942,630) pp. 43 #230.
Rudy J. Crespin, et al., "Establishing World Wide Web Presence: Guidelines for Health Care Organizations," 1996 Annual HIMSS Conference and Exhibition (IDS U.S. Appl. No. 11/942,630) pp. 43 #233.
Ruediger Simon, "DICOM: State of the Standard in 1999," undated.
Sara Lafrance, "Security vs. Access: A New Health Care Dilemma," 1996 Annual HIMSS Conference and Exhibition pp. 40 #165.
Selections from: Picture Archiving and Communication Systems (PACS) in Medicine, Huang et al, Copyright 1991. (IDS U.S. Appl. No. 11/942,630) pp. 9 #137.
Senographe 2000 D Review WorkStation DICOM V3.0 Conformance Statement, GE Medical Systems, Copyright 1999-2003. (IDS U.S. Appl. No. 11/942,630) pp. 55 #119.
Siemens Health Services, Sienet MagicRead Film Digitizers. (IDS U.S. Appl. No. 11/942,630) pp. 57 #170.
Siemens Health Services, Sienet MagicStore Classic / Sienet MagicStore Advance / P Advance: Information Management, Image Storing and Archiving System.
Siemens Health Services, Sienet MagicView Software Version VA31. (IDS U.S. Appl. No. 11/942,630) pp. 57 #168.
Siemens Medical Systems, Inc., ACOM.CONVERT DICOM Conformance Statement (Sep. 15, 1999).
Siemens Medical Systems, Inc., ACOM.M/B 2.2 BASIC System DICOM Conformance Statement (May 21, 1999).
Siemens Medical Systems, Inc., ACOM.Report VA02A DICOM Conformance Statement (Dec. 21, 2001).
Siemens Medical Systems, Inc., ACOM.Web VA21C DICOM Conformance Statement (Mar. 21, 2001).
Siemens Medical Systems, Inc., Fast, secure, reliable Sienet Enterprise PACS (1998).
Siemens SIENET DICOM Conformance Statement MagicView 300 Version VA30A, Revision 8.0, Copyright 2000. (IDS U.S. Appl. No. 11/942,630) pp. 9 #139.
Sienet MagicStore VB22D DICOM Conformance Statement, Siemens Health Services, dated May 11, 2000.
Sienet Sky DICOM Conformance Statements Webpage, Siemens Healthcare, Copyright 2002-2008. (IDS U.S. Appl. No. 11/942,630) pp. 54 #111.
Stan Wiebe, "Information Systems Planning for an Urban/Rural Integrated Delivery System," 1996 Annual HIMSS Conference and Exhibition (IDS U.S. Appl. No. 11/942,630) pp. 43 #220.
Steinhart Medizinsysteme, Product Information: Hipax System: Medical Image Processing and Communication pp. 22 #18.
The Evolution of Electronic Imaging in the Medical Environment, BJ Erickson and NJ Hangiandreou, Journal of Digital Imagining, 11:3, Supp 1, Aug. 1998.
Thomas G. Tape, MD, et al., "Designing a Clinician User-Interface for a Health Care Information System,"1996 Annual HIMSS Conference and Exhibition (IDS U.S. Appl. No. 11/942,630) pp. 41 #184.
Tom B. Wilson, Ph.D., "Healthcare Handoffs Across a Wide Area: A Groupware Solution," 1996 Annual HIMSS Conference and Exhibition (IDS U.S. Appl. No. 11/942,630) pp. 39 #149.
TREXnet HR DICOM Media Conformance Statement, Trex Medical Corp., dated Jun. 29, 1998.
UCSF Radiological Informatics Research: A Progress Report, Feb. 1996 (IDS U.S. Appl. No. 11/942,630) pp. 9 #143.
UCSF Radiological Informatics Research: A Progress Report, Feb. 1997 (IDS U.S. Appl. No. 11/942,630) pp. 9 #144.
User Manual for MEDIMAGE: DICOM Archiving & Viewing Station, Vepro Computersysteme, dated May 9, 2000. (IDS U.S. Appl. No. 11/942,630) pp. 51 #51.
User's Guide for ImageAXS Pro-Med (Windows), Digital Arts & Sciences, Copyright 1998. (IDS U.S. Appl. No. 11/942,630) pp. 50 #40.
User's Manual for Medical Imaging and Communication System (Version 3), HiPax, Copyright 2000. (IDS U.S. Appl. No. 11/942,630) pp. 50 #37.
Vepro Computersysteme GmbH, "Cardio-Viewing Station," dated 1997 (IDS U.S. Appl. No. 11/942,630) pp. 31 #3.

(56) References Cited

OTHER PUBLICATIONS

Vepro Computersysteme GMBH, MEDIMAGE The Image Management System—ACOM.Convert DICOM Archiving & Viewing Station , Software Vers. 4.42 (May 9, 1999).
Vepro Computersysteme GMBH, MEDIMAGE The Image Management System—DICOM Archiving & Viewing Station, Software Version 4.42 (Jan. 26, 2000).
Vepro Computersysteme GMBH, MEDIMAGE The Image Management System—Digital Film Recording Station, Software Version 4.40 (Oct. 28, 1999).
Vepro Computersysteme GmbH, MEDIMAGE: DICOM Archiving & Viewing Station, Software Vers. 4.42, User-Manual, dated May 9, 2000.
Vepro, Cardio-Network, dated Feb. 19, 1999 pp. 14 #39.
Vepro, Product Sheet: Image/Film Archive Server, dated Feb. 19, 1999 (IDS U.S. Appl. No. 11/942,630) pp. 14 #37.
Vepro, Product Sheet: Image/Film Jukebox Server, dated Feb. 19, 1999 (IDS U.S. Appl. No. 11/942,630) pp. 14 #36.
Vepro, Viewing Software Handbook, Viewing Software Version 4.41 (Oct. 7, 1998). (IDS U.S. Appl. No. 11/942,630) pp. 59 #203.
Voxar, Plug 'n View 3d, "What is 'Plug 'n View 3d'?" (IDS U.S. Appl. No. 11/942,630) pp. 32 #25.
Web Technology and its Relevance to PACS and Teleradiology, W DeJarnette, Applied Radiology, dated Aug. 2000. (IDS U.S. Appl. No. 11/942,630) pp. 9 #148.
William F. Andrew, ME, PE, et al., "The Computer-Based Patient Record: An Essential Technology for Healthcare," 1996 Annual HIMSS Conference and Exhibition (IDS U.S. Appl. No. 11/942,630) pp. 41 #183.
Kleinholz L et al: "Multimedia and PACS. Setting the Platform for Improved and New Medical Services in Hospitals and Regions" Car '96 Computer Assisted Radiology. Proceedings of the International Symposium on Computer and Communication Systems for Image Guided Diagnosis and Therapy, Paris, France, Jun. 1996, pp. 313-322, XP002083080 1996, Amsterdam, Netherlands, Elsevier, Netherlands ISBN: 0-444-82497-9.
Medical Imaging Magazine, Jan. 2000. Product Showcase, Automated Dicom Exchange Station. 1 page.
Terry May, "Medical Information Security: The Evolving Challenge", © 1998, IEEE doc #0-7803-4535-5/98, pp. 85-92.
Ted Cooper, "Kaiser Permanente Aniticipates High Cost as it Gears up for HIPPA", IT Health Care Strategist, vol. 1, No. 10, Oct. 1999, p. 4.
Haufe G. et al., "Pacs at Work: A Multimedia E-mail Tool for the Integration of Images, Voice and Dynamic Annotation", Computer Assisted Radiology, Proceedings fo the International Symposium, 1996 Elsevier Science B.V., pp. 417-420.
Bitcache, drupal.org, 2 pages.
European Response to the Communication Pursuant to Rule 161(1) and 162 EPC, dated May 13, 2011.
Ferelli, Mark, Content-addressable storage—Storage as I See it, Computer Technology Review, http://findarticles.com/p/articles/mi_mOBRZ/is_10_22/ai_98977101/, Oct. 2002, in 2 pages.
Menezes A et al.: "Handbook of Applied Cryptography, Key Management Techniques" Handbook of Applied Cryptography, Jan. 1, 1996, pp. 543-590.
HoneyComb Fixed Content Storage, Solaris, http://hub.opensolaris.org/bin/view/Project+honeycomb/Webhome, Oct. 26, 2009 in 2 pages.
International Search Report and Written Opinion issued in PCT/US2009/054799, dated Nov. 16, 2009.
International Search Report and Written Opinion issued in PCT/US2009/061890, dated Dec. 10, 2009.
International Search Report and Written Opinion issued in PCT/US2011/033647, dated Nov. 28, 2011.
International Search Report and Written Opinion issued in PCT/US2011/063987, dated Sep. 6, 2012.
Mellor, Chris, Making a Hash of File Content, Techworld, http://features.techworld.com/storage/235/making-a-hash-of-file-content/?, Dec. 3, 2009, in 2 pages.
Quinlan, S., et al., Venti: a new approach to archival storage, doc.cat-v.org/plan_9/4th_edition/papers/venti, in 20 pages.
Rhea, S., et al., Fast, Inexpensive Content-Addressed Storage in Foundation, http://doc.cat-v.org/plan_9/misc/foundation/, in 22 pages.
Fintan J McEvoy et al.: "Security of Patient and Study Data Associated with DICOM Images when Transferred Using Compact Disc Media" Journal of Digital Imaging; The Journal of the Society for Computer Applications in Radiology, vol. 22, No. 1, 21 Aug. 2007 (pp. 65-70).
Tolia, N., et al., Opportunistic Use of Content Addressable Storage for Distributed File Systems, USENIX Association, Jun. 9, 2003, in 15 pages.
Twisted Storage, http://twistedstorage.sourceforge.net/index.html, in 7 pages.
Twisted Storage, http://twistedstorage.sourceforge.net/news.html, in 1 page.
Candelis website excerpt, http://www.candelis.com via the Internet Wayback Machine (Archive.org), Jul. 19, 2010.
Carestream website excerpt, http://carestreamhealth.com via the Internet Wayback Machine (Archive.org), Nov. 20, 2010.
eMix website excerpt, http://www.emix.com via the Internet Wayback Machine (Archive.org), Jul. 10, 2011.
GE Healthcare IT website excerpt, http://www.dynamic-imaging.com via the Internet Wayback Machine (Archive.org), Jan. 27, 2010.
HeartIT website excerpt, http://heartit.com via the Internet Wayback Machine (Archive.org), Jan. 29, 2009.
Infinitt North America website excerpt, http://infinittna.com via the Internet Wayback Machine (Archive.org), Feb. 28, 2009.
InSite One website excerpt, http://www.insiteone.com via the Internet Wayback Machine (Archive.org), Aug. 8, 2010.
lifeIMAGE website excerpt, http://www.lifeimage.com via the Internet Wayback Machine (Archive.org), Nov. 4, 2010.
McKesson website excerpt, http://www.mckesson.com via the Internet Wayback Machine (Archive.org), Oct. 20, 2010.
MyMedicalRecords.com website excerpt, http://www.mymedicalrecords.com via the Internet Wayback Machine (Archive.org), Aug. 1, 2010.
PACS Image website excerpt, http://www.pacsimage.com via the Internet Wayback Machine (Archive.org), Apr. 2, 2010.
ScImage website excerpt, http://www.scimage.com via the Internet Wayback Machine (Archive.org), Sep. 27, 2010.
See My Radiology website excerpt, http://www.seemyradiology.com via the Internet Wayback Machine (Archive.org), Jul. 11, 2010.
Symantec Health Press Release, http://www.symantec.com/about/news/release/article.jsp?prid=20100819_01, Aug. 19, 2010.
Xrayline website excerpt, http://www.xrayline.com via the Internet Wayback Machine (Archive.org), Oct. 13, 2010.

\* cited by examiner

PERSONAL INFORMATION SYSTEM

RELATED APPLICATION

This application is a continuation of U.S. application Ser. No. 11/591,889, filed Nov. 2, 2006, which claims a benefit of U.S. application Ser. No. 09/781,605, filed Feb. 12, 2001, which claims a benefit of priority of the provisional patent application Ser. No. 60/181,985, titled "Medical Information System" and filed Feb. 11, 2000. The full disclosures of the aforementioned provisional and non-provisional applications are hereby incorporated herein by reference in their entireties for all purposes.

BACKGROUND OF THE INVENTION

1. Field of the Invention

This invention relates generally to an information system. More particularly, the invention relates to systems and methods for providing personal information including medical information using portable compact disc storage media, ubiquitous personal computers, and Internet browsers.

2. Description of the Related Art

The advantages of storing medical information on portable devices such as smartcards have been widely publicized. Storing medical information on portable devices enables one to carry on one's person potentially life-saving medical information. Healthcare providers such as emergency medical technicians can have immediate access to personal medical data such as drug allergies in emergency situations. However, despite the well-recognizable benefits, carrying one's personal data including medical data has not become a widespread practice.

There are several reasons for this phenomenon. For example, while portable devices such as smartcards can be used to store medical data, they require special equipment to read from and to write thereon. The special equipment is not a typical component of the ubiquitous personal computer (PC) thereby limiting the usefulness and the benefit of the smartcards. Additionally, due to limited use, the cost of the smartcards has not been reduced to the same extent as, for example, the compact disc (CD) including compact disc read only memory (CD ROM), compact disc recordable (CD R), compact disk recordable and writable (CD RW). CDs are used in many industries to store large amounts of data including audio, video, as well as text in a cost effective manner. Likewise, equipment to read CDs, such as a CD drive, is widely available and has become a standard component of the ubiquitous PC.

Other devices such as floppy disks pose problems as well. For example, these devices are not truly portable. They cannot be carried easily and conveniently in a wallet, for example. They require a special carrying gadget resulting in inconvenience, and thereby reducing the likelihood that they would be carried at all. Moreover, with the popularity and the reduced cost of CDs, floppy disks and the associated drives are becoming obsolete and are being replaced by the CD technology.

An additional factor contributing to the lack of widespread use of the portable devices is the method of storing, retrieving, and updating the personal data on the portable devices. Currently, the personal data that are typically stored on the portable devices are predetermined as to content. An individual patient normally does not have the option or the ability to customize the personal data that he/she desires to carry on these portable devices.

This lack of flexibility is the outcome of the industry practice and also the use of special access software programs to update the personal data. Industry practice is to generally provide a predetermined set of data on these storage devices. The purpose of the standardization is to facilitate and make implementation and maintenance of the storage devices easier. This ease, however, has come at the cost of losing flexibility. Furthermore, storing, retrieving, and updating the data on these portable devices require the use of special software programs, which are generally provided or sold to institutions and not to individual patients. Lack of access to the personal data for the individuals makes use of the portable personal data storage devices less desirable, and therefore, less widespread.

There exists a need for a system and method that resolve the shortcomings of these methods and systems.

SUMMARY OF THE INVENTION

The present invention provides systems and methods to realize the potential benefit of portable storage devices by taking advantage of standard PCs, cost effective optical disks, such as, for example, CDs and digital video discs (DVDs), and the Internet. As used herein, a standard PC or ubiquitous PC is defined as any personal computer including an optical disk drive capable of reading an optical disk, such as a CD or a DVD.

The present invention provides a personal information system comprising a subscriber computer with an optical disk drive, a portable optical disk readable by the optical disk drive, a database management server, an optical disk writer, and a subscriber interface to view the personal data stored on the portable optical disk. The optical disk writer is used to write personal data stored on the database management server onto the portable optical disk.

One embodiment of the present invention comprises a subscriber. A subscriber is any person or entity that subscribes to a service that provides and maintains personal data on a central database server accessible via the Internet. The personal data may include, for example, demographics, an image of the patient, insurance information, driver license number, social security number, emergency contact information, medical conditions, medical history, current medications, drug allergies, blood types, x-ray images, lab reports, a living will, a power of attorney, or conditions of admission to a medical facility. This is an example list of different types of data. It is contemplated that other types of data can be included, and the present invention is not limited to particular types of data. The personal data may be stored and viewed in a variety of formats including text, audio, images, and/or video formats. A subscriber may be an individual patient, a physician's office or a healthcare service center. The healthcare service center can include, for example, a hospital or a clinic.

One embodiment also comprises a subscriber system including an optical disk drive. In the case where the subscriber is an individual patient, the subscriber system would likely be a typical home PC. In the case where the subscriber is a physician's office, the subscriber system is also likely to be a PC. In the case where the subscriber is a healthcare service center such as a hospital, the subscriber system would likely be a central computer system serving one or more local area networks (LAN), each LAN serving a different department within the hospital, for example. One embodiment also comprises a communication network, such as the Internet, to which the subscriber systems may be networked. One embodiment also includes a database management server networked to the Internet.

In one embodiment, an individual patient provides personal data to a healthcare service center. The healthcare service center then creates a portable optical disk for the patient to carry, if he/she so desires. In one embodiment, the portable optical disk comprises a credit-card sized CD ROM card. U.S. Pat. No. 5,982,736, titled TRADING CARD OPTICAL COMPACT DISC—METHOD OF USING AND FORMING SAME, which is incorporated herein in its entirety by reference, discloses a process for creating credit-card sized CD ROM cards. Accordingly, those of ordinary skill in the art will understand how to create credit-card sized CD ROM cards.

The personal data that is written onto the portable optical disk is readable and updateable by the individual patient using his/her PC with an optical disk drive and connected to the Internet. The individual patient can choose to become a subscriber after receiving his/her optical disk from the healthcare service provider. The individual patient subscriber can choose to update his/her personal data on the optical disk and can receive a new portable optical disk that includes the update. The new optical disk containing the latest update is created and delivered to the patient subscriber by the database management server.

In another embodiment, an individual patient becomes a subscriber directly with the service that maintains the personal data on the database management server rather than becoming a subscriber via the healthcare service center. The patient subscribes to the database service using his/her PC connected to the Internet. The patient enters his/her personal data using his/her PC connected to the Internet. The database management server receives the personal data, creates a portable optical disk containing the personal data provided by the individual patient and delivers the portable optical disk to the patient. As in the previous embodiment, the personal data that is written onto the portable optical disk is readable and updateable by the individual patient subscriber using his/her PC, which includes an optical disk drive. The subscriber can choose to receive an updated optical disk from the database management server at any time.

In another embodiment, an individual patient subscriber provides the personal data to a healthcare service center. The healthcare service center then creates a portable optical disk and delivers it to the patient. In this embodiment, the healthcare service center can maintain the updates to the patient's personal data within its own database.

In another one embodiment, the patient updates his/her personal data by accessing the healthcare service center web site rather than by accessing the database management server web site. Additionally, the healthcare service center does not produce any optical disks. Rather, all optical disks are produced by database management server.

BRIEF DESCRIPTION OF THE DRAWINGS

These and other features will now be described with reference to the drawings summarized below. These drawings and the associated description are provided to illustrate various embodiments of the invention, and not to limit the scope of the invention. Like reference numbers represent corresponding components throughout.

DETAILED DESCRIPTION OF THE EMBODIMENTS

In the following description, reference is made to the accompanying drawings, which form a part hereof, and which show, by way of illustration, specific embodiments or processes in which the invention may be practiced. Where possible, the same reference numbers are used throughout the drawings to refer to the same or like components. In some instances, numerous specific details are set forth in order to provide a thorough understanding of the present invention. The present invention, however, may be practiced without the specific details or with certain alternative equivalent devices and/or components and methods to those described herein. In other instances, well-known methods and devices and/or components have not been described in detail so as not to unnecessarily obscure aspects of the present invention.

I. System Overview

Figure 1:
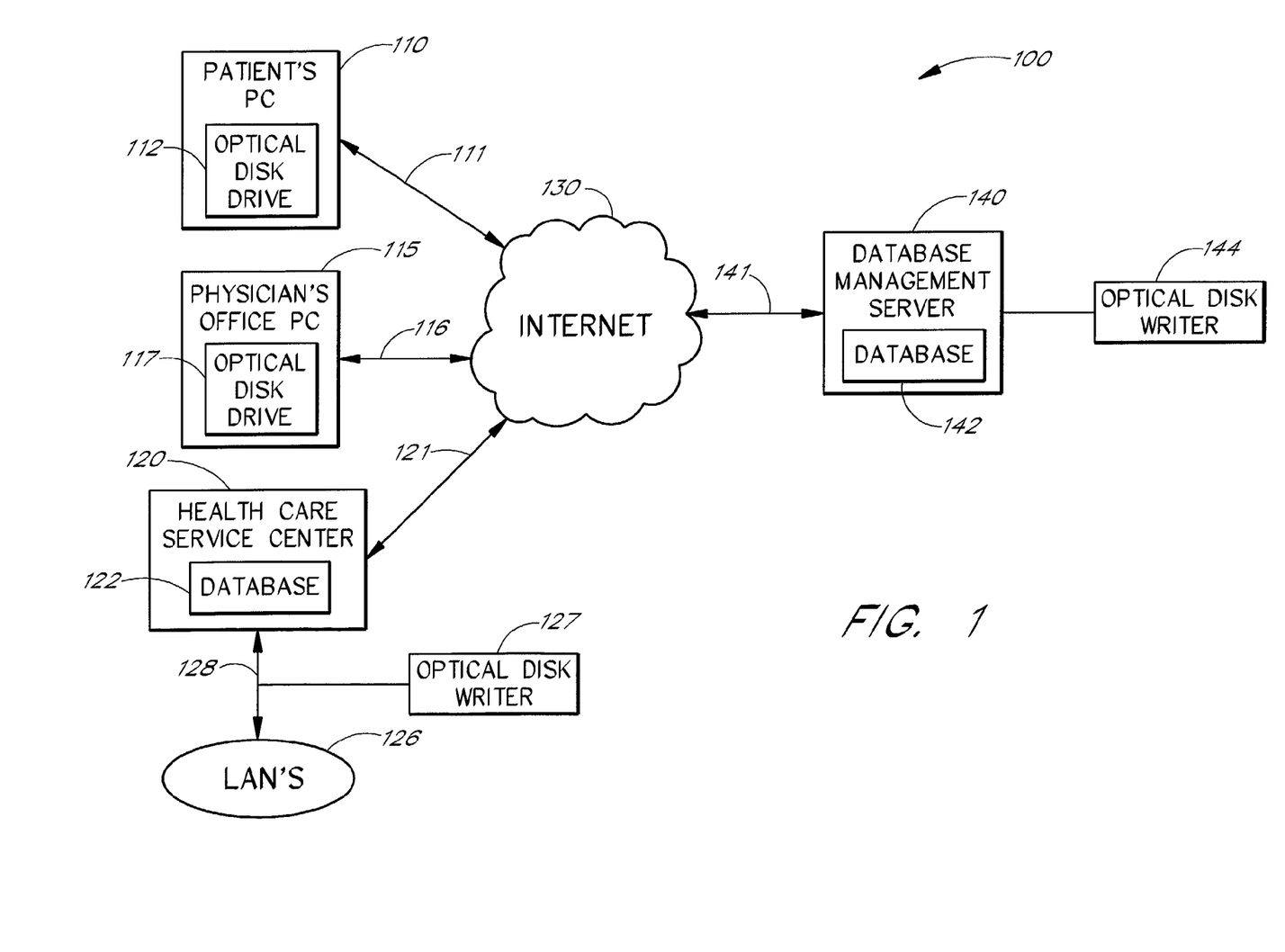
FIG. 1 illustrates a personal information system in accordance with one embodiment of the present invention.

FIG. 1 illustrates a personal information system 100 in accordance with one embodiment of the present invention. The system 100 comprises a patient's PC 100 including an optical disk drive 112, a physician's office PC 115 including an optical disk drive 117, a healthcare service center central computer (HSCCC) 120 including a database 122 and an optical disk writer 127, an Internet 130, and a database management server (DMS) 140 including a database 142 and an optical disk writer 144.

Referring to FIG. 1, the patient's PC 110, the physician's office PC 115, and the healthcare service center central computer 120 may all be connected to the Internet 130 via connections 111, 116, and 121, respectively. The database management server 140 is connected to the Internet 130 via the connection 141. Additionally, the healthcare service center central computer 120 may further be connected to one or more additional local area networks (LANs) 126 connected via the connection 128.

Figure 2:
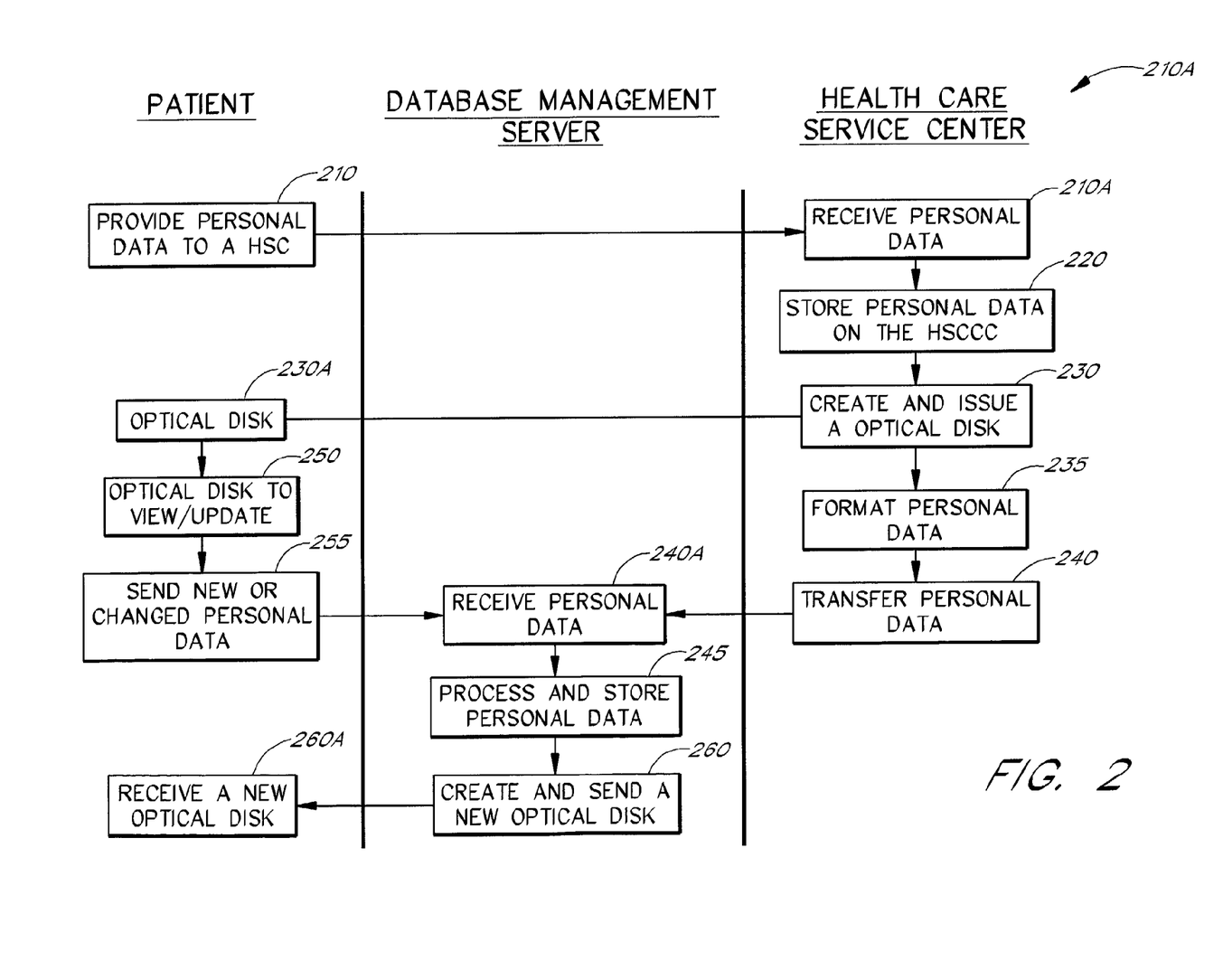
FIG. 2 illustrates a flow diagram of a process for producing portable optical disks in accordance with one embodiment of the present invention.

FIG. 2 illustrates a flow diagram of a process 200 for producing portable optical disks in accordance with one embodiment of the present invention. At a step 210, a patient provides personal data to a healthcare service center, and the healthcare service center receives the personal data at a step 210A. The patient can provide the personal data to the healthcare service center in a variety of ways. For example, the patient can provide the personal data by filling out a written form, by answering questions posed by a clerk or by electronic means. Electronic means may include, for example, downloading personal data pre-stored on the database management server 140 shown in FIG. 1 or on any electronic storage devices.

At a step 220, the personal data provided by the patient and received by the healthcare service center is stored in a database 122 residing on the HSCCC 120. The personal data received by the healthcare service center can be entered into its database 122 using an interface to a hospital information system (HIS). HIS is an information system generally installed at various hospitals. The interface used to enter the personal data into the database 122 is likely to be specific to the healthcare service center and, therefore, can be varied in its look and feel. It is contemplated that different interfaces can be used, and the invention is not limited to using any particular interface for the purpose of entering personal data into the HSCCC 120.

At a step 230, the healthcare service center can create and issue a portable optical disk, and the patient receives the portable optical disk at a step 230A. The healthcare service center can create and issue a portable optical disk to a patient any time after receiving the personal data from the patient. The portable optical disk contains the personal data and is created using the optical disk writer 127. The optical disk writer 127 can be network-connected and can be made accessible by any of the PCs connected to the LAN at the healthcare service center much like a network printer that is accessible by any of the PCs in a network. This configuration allows any PC in the network to initiate the procedure to create an optical disk.

The portable optical disk that is created and issued by the healthcare service center can contain healthcare service center-specific data or can contain generic data viewable and useable by any computer system. The personal data can be stored on the optical disk in a variety of formats. In one embodiment, the data is stored in an HTML or an XML format.

The portable optical disk can be made healthcare service center-specific not only as to the types of personal data that it contains but also as to the way the personal data can be viewed when played from an optical disk drive. The portable optical disk can contain, for example, a list of physicians affiliated with the specific healthcare service center. The portable optical disk can also contain, for example, a list of telephone numbers for the various departments within the specific healthcare service center. The portable optical disk can also contain promotional material specific to the healthcare service center as well as hotlinks to various web sites including its own web site, for example.

On the other hand, the portable optical disk can be made to contain generic data viewable and downloadable to any computer system. This configuration can provide greater flexibility and use of the optical disk. The patient can, for example, carry the portable optical disk from one healthcare service center to another without having to duplicate any of the information contained therein since any center can view and download the information into its own computer system. For instance, a generic portable optical disk can be created and issued by a hospital to a patient upon admission to the hospital for a surgery. Upon discharge from the hospital, the patient can take the portable optical disk to a physician's office wherein the physician's office can load the portable optical disk into its office PC to view, and optionally to download, the personal data that was written onto the portable optical disk. The portable optical disk can contain all the details of the surgery as well as the demographics and the insurance information, for example.

The benefit and the convenience to the patient, the physician's office, and the hospital provided by the portable optical disks are apparent. The patient need not fill out any new forms, and need not provide any insurance or any other pertinent yet duplicative information regarding his/her medical conditions or history.

In addition, the physician's office benefits since data entry efforts are minimized along with the related transcription errors. The physician's office saves time in other ways also. For example, it need not obtain pertinent medical information such as lab reports or x-rays from the hospital since they can be stored on the portable optical disk and viewable from the physician's office PC. Moreover, the physician's office can provide better service to the patient as a result of having immediate access to all the pertinent medical data. The physician's office can provide quicker service and can prevent the cost and inconvenience of duplicative tests, for example.

The hospital benefits by the use of the portable optical disks as well. Any pertinent data such as, for example, surgery details, lab reports, x-rays, can be transferred to the physician's office via the portable optical disk rather than having to manually respond to request for such information by a physician's office. As can be clearly appreciated, the convenience to all parties increases dramatically as the number of physicians visited by the patient increases.

The portable optical disk use and its benefits become even more significant when the patient moves to another area of the country or when the patient is traveling. The patient need not wait the extraordinary amount of time generally required to transfer his/her medical information from his/her previous physicians' offices or from any of the hospitals. Likewise, any pertinent data can be readily accessed from the portable optical disk that the patient is carrying during the time he/she is traveling.

Furthermore, access to the personal data on the optical disks can be controlled to provide security of the personal data contained therein. For example, the personal data may be made accessible only to authorized users who correctly enter a patient-selected password. However, since this feature may hinder emergency staff from accessing the data in an emergency, the access control feature is preferably a feature selectable by the patient on a patient-by-patient basis.

Still referring to FIG. 2, at a step 235, the HSCCC 120 can format the personal data to be transferred to the DMS 140. The HSCCC 120 may or may not format the personal data prior to transferring the data to the DMS 140. The personal data to be transferred to the DMS 140 can be in a variety of formats including HL-7, ASCII, SQL, HTML, and XML formats, for example. In one embodiment, the industry standard HL-7 format is used. The HL-7 standard describes a way of formatting data to provide consistency and usability of the data by different applications. It is contemplated that different data formats can be used, and the invention is not limited to using any particular format.

At a step 240, the HSCCC 120 connects to the Internet 130 via the connection 121 and transfers the personal data to the DMS 140. The DMS 140 receives the data at a step 240A. A session to transfer the personal data from the HSCCC 120 to the DMS 140 can be initiated by the HSCCC 120 or by the DMS 140.

For example, the session to transfer the personal data from the HSCCC 120 can be initiated by the HSCCC 120 and can occur in real-time or in a batch mode on a pre-arranged schedule. In addition, the data transfer can occur in any mode that will permit the personal data to be transferred to the DMS 140. The HSCCC 120 can, for example, dial into the DMS 140 and transfer the personal data. The HSCCC 120 can also, for example, broadcast packets of the personal data with the appropriate destination address targeted to the DMS 140.

The session to transfer the personal data from the HSCCC 120 to the DMS 140 can also be initiated by the DMS 140. As in the case where the data transfer is initiated by the HSCCC 120, the data transfer can occur in real-time or in a batch mode and can occur in any mode that will permit the personal data to be transferred to the DMS 140. The DMS 140 can, for example, dial into the HSCCC 120, retrieve the awaiting personal data, and transfer it. The DMS 140 can also, for example, remain in a polling mode and extract the data intended for the DMS 140.

Furthermore, the transfer of personal data preferably occurs in a secure mode in compliance with various security standards including the RSA 5 Secure Socket Layer (SSL) protocol. The RSA 5 SSL protocol uses 128 bit encryption on all information sent to and from the DMS 140. In addition, the data stored in the database 142 can be encrypted using the Desktop Encryption Standards (DES), DES III or Blowfish. It is contemplated that different encryption methods can be used, and the invention is not limited to using any particular encryption method.

The security of data is also preferably maintained in compliance with the Health Information Portability and Accountability Act (HIPAA). The HIPAA legislation was passed to mandate a certain level of security to protect the health and medical information that have become widely available in electronic formats transmittable over public networks such as the Internet.

At a step 250, the patient can play the portable optical disk on his/her PC to review the information contained therein. In one preferred embodiment, the optical disk can auto-play into an Internet web browser such as, for example, Microsoft Internet Explorer or the Netscape Navigator. The optical disk can auto-play into the web browser and display the personal data stored therein. In addition, the optical disk can contain other navigational tools such as hotlinks to various web sites including the web site of the healthcare service center that issued the optical disk or the database management server web site. By using the hotlinks provided on the optical disk, the patient can, for example, conveniently upload updates of the personal data to the DMS 140 at a step 255. The patient can also pre-register for a hospital admission, for example, using the hotlinks provided on the optical disk.

The access to the personal data stored in the database 142 can be controlled by various methods to provide data security. For example, Verisign Certificate Authentication can be used to verify the patient and the information being transmitted to and from the patient's PC 110. A patient-specific identification number such as a pre-assigned medical record number and/or a social security number may be used to access the patient's records. Other technologies such as embedding and verifying the fingerprints on the optical disk may be incorporated to provide significant levels of patient authentication. It is contemplated that different methods can be used to control access to the personal data stored in the database 142, and the invention is not limited to using any particular method.

Still referring to FIG. 2, at a step 245, the database management server 140 can process the personal data that it receives from the healthcare service center central computer 120 in preparation for storage into its database 142. The DMS 140 can, for example, parse the personal data that it receives and store the data as an HTML or an XML document into the database 142 if not already in the HTML or the XML format. In a preferred embodiment, the DMS 140 stores the personal data as an HTML or an XML document into the database 142.

At a step 260, the database management server 140 can create a new optical disk containing the updates sent by the patient using the optical disk writer 144. The new optical disk is delivered and received by the patient at a step 260A. As in the case where the healthcare service center creates the optical disk, the optical disk writer 144 can be network-connected to enable the procedure to initiate creating the optical disk from any PC on the Database Management Server network. The optical disk creation process can also be fully automated using robotics technology. Robotics technology can be implemented with either of the optical disk writers 127 or 144 to automate the optical disk writing process, the labeling process, the packaging process, and the shipment process, for example.

The patient can repeat the steps 250 and 255 at any time to update his/her personal data. The patient may, but is not required to, request a new optical disk that reflects the latest updates that he/she provides to the DMS 140. Furthermore, the healthcare service center central computer 120 may at any time connect to the database management server 140 to download the latest personal data stored on the DMS 140.

In one embodiment, the personal data is provided by the patient directly to the database management server 140 rather than first providing the data to a healthcare service center which in turn forwards the data to the DMS 140. The DMS 140 receives the personal data from the patient, creates, and delivers an optical disk to the patient. Referring to FIG. 2, this embodiment could be depicted by deleting the Healthcare Service Center column and starting the process from the step 255.

At the step 255, the patient can send new and/or changed personal data to the DMS 140. The DMS 140 receives the sent data at the step 240A, processes and stores the personal data at the step 245. At the step 260, the DMS can create and send a new optical disk to the patient who receives the new optical disk at the step 260A. The patient can repeat this process at any time to forward new and/or changes to the personal data that is stored on the DMS 140.

In another embodiment, the personal data is completely contained within the healthcare service center and all related processing of the data occurs within the healthcare service center. This embodiment provides increased data security since no personal data is transferred outside the healthcare service center central computer 120.

Figure 3:
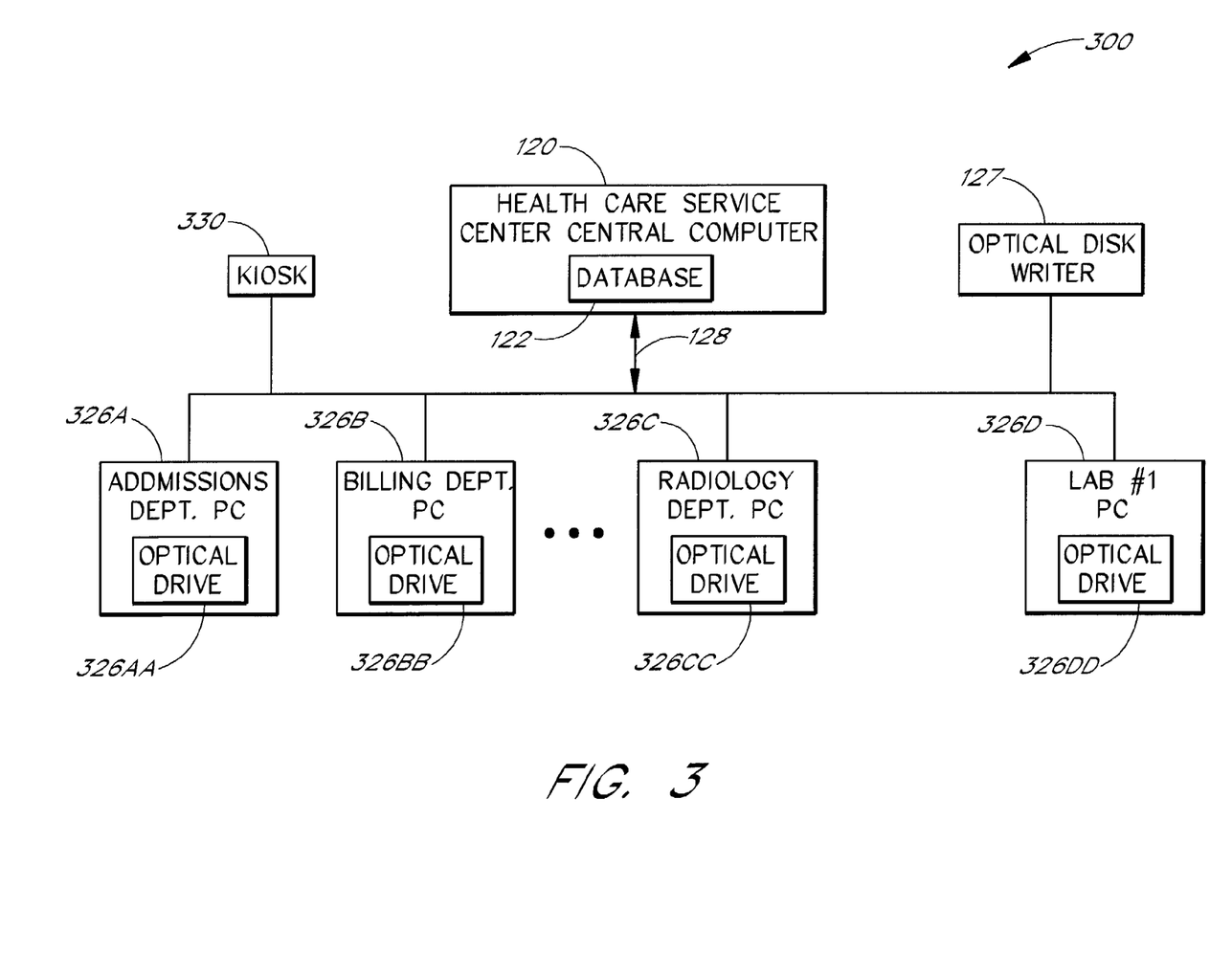
FIG. 3 illustrates a personal information system in accordance with one embodiment of the present invention.

FIG. 3 illustrates a personal information system 300 in accordance with one embodiment of the present invention. The system 300 comprises a healthcare service center central computer 120 including a database 122, an internal network backbone 128, a network-connected optical disk writer 127, a kiosk 330, and various department PCs as exemplified by the Admissions department PC 326A, the Billing department PC 326B, the Radiology department PC 326C, and the Lab #1 PC 326D. Each of the department PCs contain an optical disk drive. Moreover, any of these departments, as well as any other departments within the healthcare service center, can be served by its own LAN. For example, the Admissions department can be served by a separate LAN that consists of a number of PCs including the PCs installed at each Admissions registration desk as well as the PCs in the various cubicles and the offices within the Admissions department. The Admissions department LAN can, in turn, be connected to the healthcare service center's internal network backbone via various bridges and/or routers, as appropriate.

Referring to FIG. 2, the process for creating portable optical disks used in connection with the system 300 could be depicted by deleting the Database Management Server column. As in the process 200, a patient provides the personal data to the healthcare service center, which stores the data in the database 122 of its healthcare service center central computer 120. The healthcare service center then creates and issues an optical disk to the patient.

In contrast to the process 200, the patient using the system 300 cannot update the personal data by connecting to the database management server 140 via the Internet since the central database of personal data is maintained at the database 122 to increase data security. However, the healthcare service center may provide a kiosk 330 that includes a user interface. The patient can use the interface to enter updates to the personal data that is stored on the database 122. The user interface provided at the kiosks can be displayed in a variety of formats. The healthcare service center can setup a number of kiosks at various locations throughout the healthcare service center for the patients' use and convenience. The kiosks may also include an optical disk drive to allow the patient to view the information stored on the optical disk as well.

As in the process 200, the healthcare service center will create and issue the initial optical disk, but the healthcare service center will also create and issue new optical disks that reflect any additions or changes to the personal data.

In another embodiment, the patient updates his/her personal data by accessing the healthcare service center web site rather than by accessing the database management server 140. Additionally, the healthcare service center does not produce any optical disks and all optical disks are produced by an offsite database management server.

Figure 4:
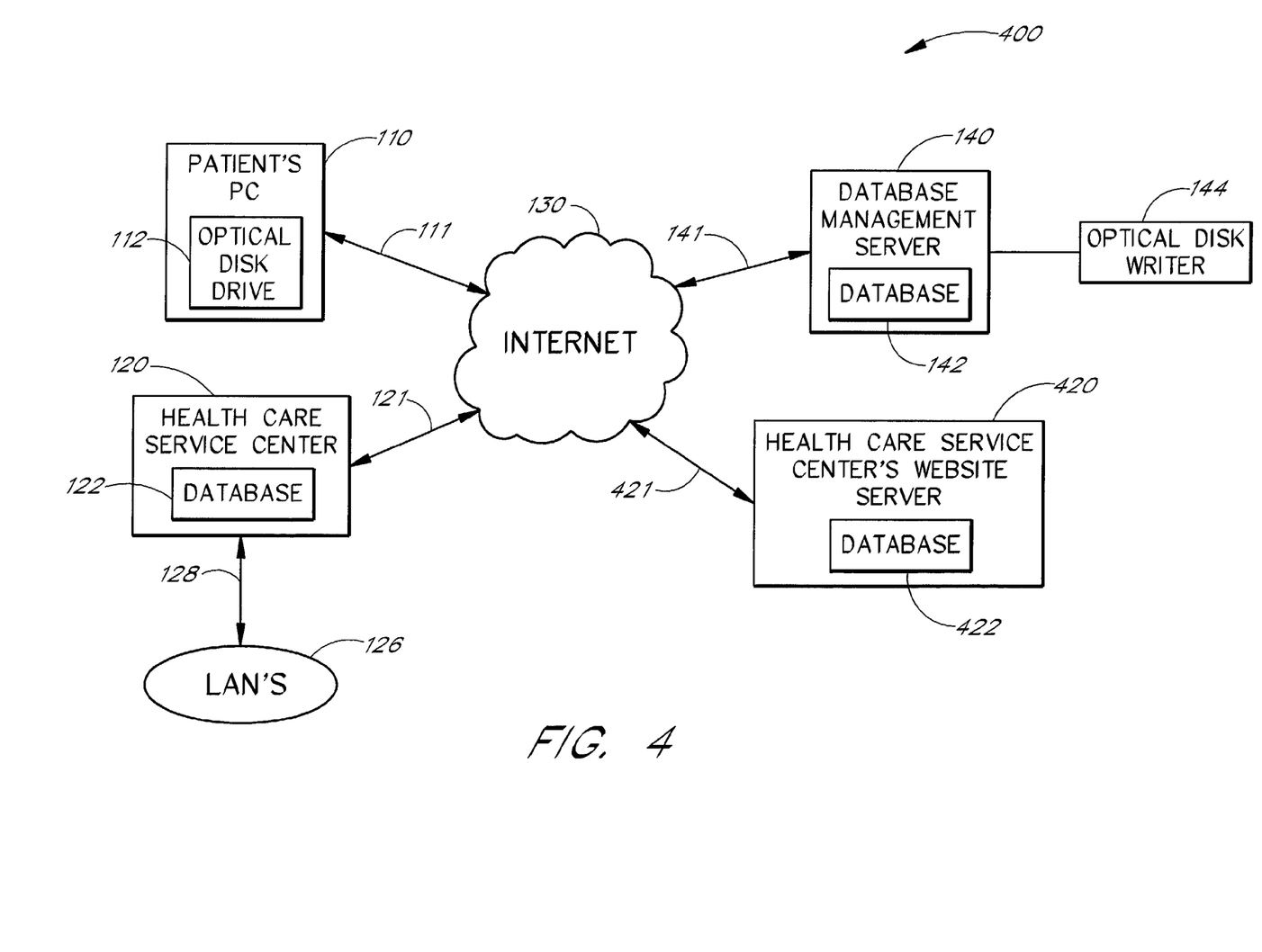
FIG. 4 illustrates a personal information system in accordance with one embodiment of the present invention.

FIG. 4 illustrates a personal information system 400 in accordance with one embodiment of the present invention. The system 400 comprises a patient's PC 110 including an optical disk drive 112 and connected to the Internet 130 via the connection 111. The system 400 further comprises a healthcare service center central computer 120 including a database 122 and connected to the Internet 130 via the connection 121, an internal network backbone 128, one or more LANs 126, a database management server 140 including a database 142 and a network-connected optical disk writer 144 and connected to the Internet 130 via the connection 141, and a healthcare service center web site server (HSCWSS) 420 including a database 422 and connected to the Internet 130 via a connection 421.

In the system 400, the patient provides the personal data to the healthcare service center which is in turn stored in the database 122. The database management server 140 thereafter either receives or retrieves the personal data stored in the database 122, as in the process 200. The DMS 140 then creates and delivers an optical disk to the patient. In contrast to the process 200, the patient receives his/her initial card from the database management server rather than the healthcare service center.

Subsequent to the receipt of his/her initial optical disk, the patient can add and/or update his/her personal data by logging onto the healthcare service center web site server 420. Any such additions and/or updates to the personal data are received and/or retrieved by the DMS 140 either in a real-time mode or in a batch mode from the healthcare service center web site server 420 via the Internet 130. The DMS 140 can create and deliver an updated optical disk to the patient if the patient so requests. The healthcare service center is not engaged in producing optical disks in the system 400 illustrated in FIG. 4.

The system 400 increases the healthcare service center's ability to build patient loyalty and to control patient information. By serving as the portal through which the patient maintains his/her information, the healthcare service center has the opportunity to expose the patient to various marketing promotions as well as maintaining a visible presence in the patient's mind. In addition, the system 400 allows the healthcare service center to maintain and access the latest data regarding on any of its patients with no additional effort on its part. Any additions and/or changes to the patient's personal data are made by the patient to the database 422, to which the healthcare service center has full access.

Furthermore, the healthcare service center can implement various schemes to control the access and the types of data that can be changed by the patient. Various access control schemes, as discussed in connection with the process 200, may be implemented to provide security. Additionally, the healthcare service center can control the types of data that may be changed. For example, the healthcare service center may prevent certain fields, such as the field designating the blood type, from being changed.

In all of the embodiments described above, the patient has flexibility to choose what information he/she decides to store and carry on the optical disk. For example, one individual may only want his/her emergency information such as drug allergies, blood type, emergency contact information, and current medical conditions. On the other hand, another individual may desire to carry a more comprehensive optical disk containing, for example, complete demographics, a power of attorney, insurance data, a video of his/her will, etc. in variety of formats including text, audio, images, and video. Still another individual may desire to store various family data and vaccination data to leave with a babysitter. Yet another individual may desire to store related information such as parental consent forms, emergency contact information to leave at a child's school. Yet another individual may store information related to skilled nursing care facility. Since the optical disk technology offers large data storage capacity in these cards, the types and the amount of information to be stored thereon is limited only by the imagination and the creativity of the individual.

Although the invention has been described in terms of certain preferred embodiments, other embodiments that will be apparent to those of ordinary skill in the art, including embodiments which do not provide all of the features and advantages set forth herein, are also within the scope of this invention. Accordingly, the scope of the invention is defined by the claims that follow.

What is claimed is:

1. A computer-implemented method for personal health data management, executing on one or more computers, said method comprising:

receiving first personal health data comprising DICOM images associated with a particular patient identity over the Internet;

in response to receiving the first personal health data, sending to a robotic optical disc burner, for collective writing on a first optical disc, the first personal health data, at least one link related to a first healthcare service center, and security data configured to instruct a viewing computer, upon receipt of a password, to provide access to the first optical disc with the first personal health data, the at least one link, and the security data written with the robotic optical disc burner;

verifying permission to store the first personal health data based on an electronic permissions input;

after the permission to store the first personal health data has been verified, storing the first personal health data in a first personal health data database at the first healthcare service center;

after the first personal health data has been stored and the permission to store the first personal health data has been verified, sending, via the Internet, the first personal health data to a remote database management server;

parsing and converting at least a portion of the first personal health data into an XML format; and providing secure access to the first personal health data to a second healthcare service center distinct from the first healthcare service center.

2. The method of claim 1, wherein receiving the first personal health data comprises receiving the first personal health data from a pre-loaded database containing patient information.

3. The method of claim 1, wherein sending the first personal health data comprises transmitting the first personal health data to the remote database management server using encryption.

4. The method of claim 3, wherein the encryption comprises a Secure Socket Layer (SSL) protocol.

5. The method of claim 1, wherein sending, via the Internet, the first personal health data to the remote database management server further comprises:
   receiving an electronic request from the remote database management server for the first personal health data stored in the first personal health data database;
   verifying that the remote database management server has permission to access the first personal health data; and
   after verifying the remote database management server has permission to access the first personal health data, transmitting to the first personal health data stored in the first personal health data database to the remote database management server.

6. The method of claim 1, wherein the first personal health data further comprises medical reports.

7. The method of claim 1, wherein the remote database management server is further configured to allow a second optical disc comprising the first personal health data to be burned.

8. The method of claim 1, wherein the method further comprises:
   receiving, from the remote database management server, second personal health data, distinct from the first personal health data, associated with the particular patient identity.

9. A system, comprising one or more computers, for personal health data management, said system comprising:
   a robotic optical disc burner;
   a first computer associated with a first personal health data database, said first computer configured to:
      receive first personal health data comprising DICOM images associated with a particular identity over the Internet;
      in response to reception of the first personal health data, send to the robotic optical disc burner, for collective writing on a first optical disc, the first personal health data, at least one link related to a healthcare service center, and security data configured to instruct a viewing computer, upon receipt of a password, to provide access to the first optical disc with the first personal health data, the at least one link, and the security data written with the robotic optical disc burner;
      verify permission to store the first personal health data based on an electronic permissions input,
      after the permission to store the first personal health data has been verified, store the first personal health data in the first personal health data database; and
      after the first personal health data has been stored and the permission to store the first personal health data has been verified, send, via the Internet, the first personal health data to a remote database management server,
   a remote database management server configured to receive the first personal health data, via the Internet, from said first computer, after the first personal health data has been stored and the permission to store the first personal health data has been verified, said remote database management server further configured to:
      parse and convert at least a portion of the first personal health data into an XML format, and,
      provide secure access to the first personal health data to the healthcare service center.

10. The system of claim 9, wherein the computer is further configured to receive second personal health data related to a second particular identity distinct from the particular identity, and send the second personal health data to the robotic optical disc burner to be burned onto a second optical disc.

11. The system of claim 9, wherein the robotic optical disc burner is further configured to write optical discs that are configured to auto-execute once inserted into a personal computer.

12. The system of claim 9, wherein the first computer is configured to receive the first personal health data from a pre-loaded database containing patient information.

13. The system of claim 9, wherein the first computer is further configured to:
   receive an electronic request from the remote database management server for the first personal health data stored in the first personal health data database;
   verify that the remote database management server has permission to access the first personal health data; and
   after verifying the remote database management server has permission to access the first personal health data, provide access to the first personal health data stored in the first personal health data database to the remote database management server.

14. The system of claim 9, wherein the first computer is further configured to:
   send the first personal health data to the remote database management server using encryption.

15. The system of claim 9, wherein the encryption comprises a Secure Socket Layer (SSL) protocol.

16. The system of claim 9, wherein the first personal health data further comprises medical reports.

17. A non-transient computer-readable medium comprising computer-executable instructions for personal health data management, said computer-executable instructions, when running on one or more computers, performing a method comprising:
   receiving first personal health data comprising DICOM images associated with a particular patient identity over the Internet;
   in response to receiving the first personal health data, sending to a robotic optical disc burner, for collective writing on a first optical disc, the first personal health data, at least one link related to a healthcare service center, and security data configured to instruct a viewing computer, upon receipt of a password, to provide access to the first optical disc with the first personal health data, the at least one link, and the security data written with the robotic optical disc burner;
   verifying permission to store the first personal health data based on an electronic permissions input;
   after the permission to store the first personal health data has been verified, storing the first personal health data in a first personal health data database;
   after the first personal health data has been stored and the permission to store the first personal health data has been verified, sending, via the Internet, the first personal health data to a remote database management server;
   parsing and converting at least a portion of the first personal health data into an XML format; and
   providing secure access to the first personal health data to the healthcare service center.

18. The non-transient computer-readable medium of claim 17, wherein the first personal health data further comprises medical reports.

19. The non-transient computer-readable medium of claim 17, wherein
sending, via the Internet, the first personal health data to the remote database management server comprises transmitting the first personal health data to the remote database management server using encryption.

* * * * *